United States Patent [19]
Johansen et al.

[11] Patent Number: 5,854,211
[45] Date of Patent: Dec. 29, 1998

[54] COMPOUNDS WITH GROWTH HORMONE RELEASING PROPERTIES

[75] Inventors: Nils Langeland Johansen, København ø; Jesper Lau, Farum; Kjeld Madsen, VærLøse; Behrend Friedrich Lundt, Kokkedal; Henning Thøgersen, Farum; Birgit Sehested Hansen, StenLøse, all of Denmark

[73] Assignee: Novo Nordisk A/S, Bagsvaerd, Denmark

[21] Appl. No.: 464,679

[22] PCT Filed: Dec. 22, 1994

[86] PCT No.: PCT/DK94/00486

§ 371 Date: Jun. 6, 1995

§ 102(e) Date: Jun. 6, 1995

[87] PCT Pub. No.: WO95/17422

PCT Pub. Date: Jun. 29, 1995

[30] Foreign Application Priority Data

Dec. 23, 1993 [DK] Denmark ................................ 1438/93
Jan. 17, 1994 [DK] Denmark ................................ 0075/94
Jun. 30, 1994 [DK] Denmark ................................ 0781/94
Oct. 7, 1994 [DK] Denmark ................................ 1165/94

[51] Int. Cl.$^6$ .......................... A61K 38/07; A61K 38/08; A61K 38/14; C07K 7/02
[52] U.S. Cl. .................................. 514/8; 514/17; 514/18; 530/322; 530/329; 530/330

[58] Field of Search .................................... 514/8, 17, 18; 530/330, 329, 322

[56] References Cited

U.S. PATENT DOCUMENTS

| | | | |
|---|---|---|---|
| 5,470,753 | 11/1995 | Sepetor et al. | 436/89 |
| 5,480,869 | 1/1996 | Wei et al. | 514/16 |
| 5,486,505 | 1/1996 | Bowers et al. | 514/16 |
| 5,559,209 | 9/1996 | Nishimoto | 530/326 |
| 5,602,099 | 2/1997 | Schiller et al. | 514/18 |
| 5,663,146 | 9/1997 | Bowers et al. | 514/16 |
| 5,767,085 | 6/1998 | Johansen et al. | 514/17 |
| 5,776,901 | 7/1998 | Bowers et al. | 514/16 |

*Primary Examiner*—Jeffrey E. Russel
*Attorney, Agent, or Firm*—Steve T. Zelson, Esq.; Cheryl H. Agris, Esq.

[57] ABSTRACT

Novel peptide derivatives, compositions containing them, and their use for treating medical disorders resulting from a deficiency in growth hormone are disclosed. These peptide derivatives have the formula:

$$A—B—C—D—E (—F)_p$$

wherein A, B, C, D, E, F and p are as defined in the specification. These peptides exhibit improved resistance to proteolytic degradation as well as improved growth hormone releasing activity.

15 Claims, No Drawings

COMPOUNDS WITH GROWTH HORMONE RELEASING PROPERTIES

CROSS-REFERENCE TO RELATED APPLICATIONS

This application is a 35 U.S.C. 371 national application of PCT/DK94/00486 filed Dec. 22, 1994, which is incorporated herein by reference.

FIELD OF INVENTION

The present invention relates to novel peptide derivatives, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration nonviable. Furthermore, other directly acting natural secretagogues, e.g., GHRH and PACAP, are longer polypeptides for which reason oral administration of them is not viable.

The use of shorter peptides for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711 and WO 93/04081.

The composition of growth hormone releasing peptides or peptide derivatives is important for their growth hormone releasing potency as well as their bio-availability. It is therefore the object of the present invention to provide peptides with growth hormone releasing properties which have improved properties relative to known peptides of this type.

SUMMARY OF THE INVENTION

Accordingly, the present invention relates to a compound of general formula I

A—B—C—D—E(—F)$_p$ wherein
p is 0 or 1;
A is imidazolyl-$C_{1-6}$-alkanoic acid, imidazolyl-$C_{1-6}$alkenoic acid, amino-$C_{1-6}$alkanoic acid or amino-$C_{1-6}$alkenoic acid or a L- or D- α-amino acid selected from the group consisting of H-His, H-Ala, H-D-Ala, H-(β-alanine), H-Aib, sarcosine and Gly;
B is D-Trp, D-2Nal or D-Phe;
C is Ala, Ser or Gly;
D is Trp, Phe, β-(2-Thienyl)-alanine, or N-aralkyl glycine;
E, when p is 1, is D-Phe, or, when p is 0, E is —NH—CH(CH$_2$—R$^3$)—CO—R$^4$ or —NH—CH(CH$_2$—R$^3$)—CH$_2$—R$^4$, wherein
R$^3$ is phenyl,
and R$^4$ is piperazino, morpholino, piperidino, —OH or —N(R$^5$)R$^6$, wherein each of R$^5$ and R$^6$ is independently hydrogen or lower allyl;
F, when p is 1, is —NH—CH(R$^{10}$)—(CH$_2$)$_v$—R$^7$)—, wherein
v is 0 or an integer between 1 and 8, and
R$^7$ is imidazolyl, piperazino, morpholino, piperidino or —N(R$^9$)—R$^9$, wherein each of R$^8$ and R$^9$ is independently hydrogen or lower alkyl, or the Amadori rearrangement product from an amino group and a hexapyranose or a hexapyranosyl-hexapyranose of formula

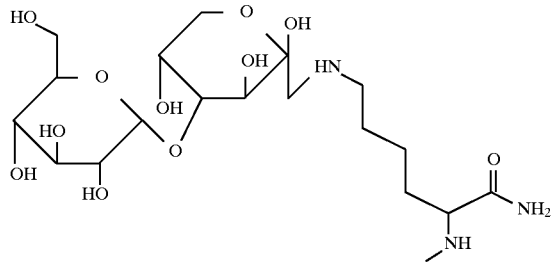

and
R$^{10}$ is —H, —COOH, —CO—R$^{11}$, CH$_2$—R$^{11}$ or —CH$_2$—OH, wherein R$^{11}$ is piperazino, morpholino, piperidino or —N(R$^{12}$)—R$^{13}$, wherein each of R$^{12}$ and R$^{13}$ is independently hydrogen or lower alkyl;
with the proviso that at least one amide bond between A and B, B and C, C and D, D and E or, when p is 1, E and F, is substituted by aminomethylene or that, when p is 0, E is NH—CH(CH$_2$—R$^3$)—CH$_2$—R$^4$ or that, when p is 1, R$^{10}$ is CH$_2$—R$^{11}$;
or a pharmaceutically acceptable salt thereof.

It is believed that peptide derivatives of formula I exhibit an improved resistance to proteolytic degradation by gastrointestinal or plasma enzymes due to the substitution of an amide bond (—CONH—) with aminomethylene (—CH$_2$NH) or by introducing an N-aralkyl glycine. The increased resistance to proteolytic degradation of the peptide derivatives of the invention is expected to improve their bioavailability compared to that of the peptides suggested in the prior literature.

In the present context, the term "lower alkyl" is intended to indicate alkyl with 1–6 carbon atoms, in particular methyl, ethyl, propyl, iso-propyl, butyl, pentyl or hexyl.

DETAILED DESCRIPTION OF THE INVENTION

In a preferred embodiment of the compound of formula I, p is 1. In another preferred embodiment of the compound of formula I, A is His, D-Ala or imidazolyl propionic acid. B is preferably D—Trp or D—2Nal. C is preferably Ala. D in the meaning of N-aralkyl glycine is preferably N-benzyl glycine. D is preferably Trp. E is preferably D-Phe. Within the meaning of F, v is preferably 3 to 6 and $R^7$ is preferably —$NH_2$. $R^{10}$ is preferably —$CONH_2$, —$CH_2OH$.

Examples of specific compounds of the invention are
H-Hisψ($CH_2NH$)D-Trp-Ala-Trp-D-Phe-Lys-$NH_2$
H-His-D-Trpψ($CH_2NH$)Ala-Trp-D-Phe-Lys-$NH_2$
H-His-D-Trp-Alaψ($CH_2NH$)Trp-D-Phe-Lys-$NH_2$
H-His-D-Trp-Ala-Trpψ($CH_2NH$)D-Phe-Lys-$NH_2$
H-His-D-Trp-Ala-Trp-D-Pheψ($CH_2NH$)Lys-$NH_2$
H-D-Ala-D-2Nal-Alaψ($CH_2NH$)Trp-D-Phe-Lys-$NH_2$
H-D-Ala-D-2Nal-Ala-Trp-D-Pheψ($CH_2NH$)Lys-$NH_2$
(3-(4-Imidazolyl)propionyl)-D-2Nal-Ala-Trp-D-Pheψ($CH_2NH$)Lys-OH
(3-(4-Imidazolyl)propionyl)-D-2Nal-Ala-Trp-D-Pheψ($CH_2NH$)Lys-$NH_2$
(3-(4-Imidazolyl)acryloyl)-D-2Nal-Ala-Trp-D-Pheψ($CH_2NH$)Lys-$NH_2$
H-D-Ala-D-Phe-Ala-Trp-D-Pheψ($CH_2NH$)Lys-$NH_2$
(2R)-(H-D-Ala-D-Phe-Ala-Trp-NH)-3-phenylpropylamine
(2S)-(H-D-Ala-D-2Nal-Alaψ($CH_2NH$)Trp-D-Phe-NH)-6aminohexanol
H-D-Ala-D-2Nal-Alaψ($CH_2NH$)Trp-D-Phe-$NH_2$
4-(H-D-Ala-D-2Nal-Alaψ($CH_2NH$)Trp-D-Phe-NH)butylamine
(2R)-(H-D-Ala-D-2Nal-Ala-Trp-NH)-3-phenylpropylamine
((2R)-(H-D-Ala-D-2Nal-Ala-Trp-NH)-3-phenylpropylamino)hexylamine
(2R)-(H-D-2Nal-Ala-N-Bzl-Gly-NH)-3-phenylpropylamine
(2R)-(H-D-Ala-D-2Nal-Ala-N-Bzl-Gly-NH)-3-phenylpropylamine
H-Aib-D-2Nal-Ala-N-Bzl-Gly-D-Pheψ($CH_2NH$)Lys-$NH_2$
(2S)-((3-(4-Imidazolyl)propionyl)ψ($CH_2NH$)D-Phe-Ala-Trp-D-Phe-NH)-6aminohexanol
(2S)-((3-(4-Imidazolyl)propionyl)-D-Pheψ($CH_2NH$)Ala-Trp-D-Phe-NH)-6aminohexanol
(2S)-((3-(4-Imidazolyl)propionyl)-D-Phe-Alaψ($CH_2NH$)Trp-D-Phe-NH)-6aminohexanol
(2S)-((3-(4-Imidazolyl)propionyl)-D-Phe-Ala-Trpψ($CH_2NH$)D-Phe-NH)-6-aminohexanol
(2S)-(2R)-((3-(4-Imidazolyl)propionyl)-D-Phe-Ala-Trp-NH)-3-phenylpropylamino)-6-aminohexanol
3-((3-(4-Imidazolyl)propionyl)-D-Trp-Alaψ($CH_2NH$)Trp-D-Phe-NH)propylamine
(2S)-((3-(4-Imidazolyl)propionyl)-D-Phe-Ala-Trp-D-Pheψ($CH_2NH$)NH)-6-aminohexanol
(2S)-((3-(4-Imidazolyl)propionyl)-D-Trp-Alaψ($CH_2NH$)Trp-D-Phe-NH)-6-aminohexanol
3-((3-(4-Imidazolyl)propionyl)-D-Trp-Alaψ($CH_2NH$)Trp-D-Phe-NH)propylamine
H-D-Ala-D-2Nal-Ala-N-Bzl-Gly-D-Pheψ($CH_2NH$)Lys-$NH_2$
H-Aib-D-2Nal-Ala-N-Bzl-Gly-D-Pheψ($CH_2NH_2$)

Abbreviations
D-2Nal: D-2-naphthylalanine
N-Bzl: N-benzylglycine
H-Aib: H-amino-isobutyric acid Compounds of formula I may be prepared by conventional methods of solution or solid phase peptide synthesis. For instance, solid phase synthesis may be carried out substantially as described by Stewart and Young, *Solid Phase Peptide Synthesis*, 2nd. Ed., Rockford, Ill., USA, 1976. Solution peptide synthesis may for instance be carried out substantially as described by Bodansky et al., *Peptide Synthesis*, 2nd. Ed., New York, N.Y., USA, 1976.

Aminomethylene as a substitution of an amide bond may be introduced according to the method described by Y. Sasaki and D. H. Coy, *Peptides* 8(1), 1987, pp. 119–121. Peptide derivatives containing a mono- or di-hexapyranose derivatised amino group may be prepared by an Amadori rearrangement substantially be the method described by R. Albert et al., *Life Sciences* 53, 1993, pp. 517–525. Examples of suitable mono- or di-hexapyranoses are glucose, galactose, maltose, lactose or cellobiose. Derivatives used as starting materials in the synthesis may be obtained commercially and may, when required, be provided with suitable protecting groups were introduced.

Pharmaceutically acceptable acid addition salts of compounds of formula I include those produced by reaction of the peptide with inorganic or organic acids such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoroacetic, sulfamic and fumaric acid.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g.

A typical tablet which may be prepared by conventional tabletting techniques may contain:

Core:
Active compound (as free compound or salt thereof) 100 mg
Colloidal silicon dioxide (Aerosil) 1.5 mg
Cellulose, microcryst. (Avicel) 70 mg
Modified cellulose gum (Ac-Di-Sol) 7.5 mg
Magnesium stearate
Coating:
HPMC approx. 9 mg
*Mywacett 9–40 T approx. 0.9 mg
*Acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants such as bile acid salts or polyoxyethylene higher alcohol ethers, absorption enhancers such as lecithin (phosphatidylcholine) or cyclodextrin, or preservatives such as parabenes.

Generally, the compounds of the present invention are dispensed in unit dosage form comprising 0.0001–100 mg of active ingredient together with a pharmaceutically acceptable carrier per unit dosage.

The dosage of the compounds according to this invention is suitably 1–500 mg/day, e.g. about 100 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. It is assumed that compounds of formula I can be administered for purposes of stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, treatment of osteoporosis, stimulation of the immune system, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral or nasal administration comprise from about 0.0001 mg to about 100 mg, preferably from about 0.001 mg to about 50 mg of the compounds of formula I admixed with a pharmaceutically acceptable carrier or diluent.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula I combined with one or more compounds exhibiting a different activity, e.g., an antibiotic or other pharmacologically active material. This may be another secretagogue such as GHRP (1 or 6) or GHRH or analogues thereof, growth hormone or an analogue thereof or somatomedins such as IGF-1 or IFG-2.

The route of administration may be any route which effectively transports the active compound to the appropriate or desired site of action, such as oral, nasal or parenteral, the oral route being preferred.

Apart from the pharmaceutical use of the compounds of formula I, they may be useful in vitro tools for investigating the regulation of growth hormone release.

The compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patient's pituitary to release growth hormone.

Compounds of formula I may be administered to commercially important animals to increase their rate and extent of growth, and to increase milk production.

Pharmacological Methods

Compounds of formula I may be evaluated in vitro for their efficacy and potency to release growth hormone in primary rat somatotrophs.

Rat primary somatotrophs may be prepared essentially as described previously (Chen et al., Endocrinology 1991, 129, 3337–3342 and Chen et al., Endocrinology 1989, 124, 2791–2798). Briefly, rats are killed by decapitation. The pituitary is quickly removed. The pituitaries are digested with 0.2% collagenase and 0.2% hyalurinidase in Hanks balanced salt solution. The cells are resuspended in Dulbecco's Modified Eagle's medium containing 0.37% NaHCO3, 10 % horse serum, 2.5% fetal calf serum, 1% nonessential amino acids, 1% glutamine and 1% penicillin/streptomycin and adjusted to $1.5 \times 10^5$ cells/ml. One ml of this suspension is placed in each well of 24-well trays and left for 2–3 days before release experiments are performed.

On day one of the experiments, cells are washed twice with the above medium containing 25 mM HEPES, pH 7.4. Growth hormone release initiated by addition of medium containing 25 mM HEPES and test compound. Incubation is carried out for 15 minutes at 37° C. After incubation growth hormone released to the medium is measured by a standard RIA.

Compounds of formula I may be evaluated for their in vivo effects on growth hormone release in pentobarbital anaesthetized female rats as described previously (Bercu et al. Endocrinology 1991, 129, 2592–2598). Briefly, adult male Sprague-Dawley rats are anesthetized with pentobarbital 50 mg/kg ip. After the rats had been fully anaesthesized the rats are implanted with a tracheal cannula and catheters in the carotid artery and the jugular vein. After a 15 minute recovery, a blood sample is taken at time 0. The pituitary secretagogues are administered by iv and artery blood samples are put on ice for 15 minutes and then centrifuged for 2 minutes at 12,000 xg. The serum is decanted and amount of growth hormone determined using a standard RIA.

The invention is further illustrated in the following examples which are not in any way intended to limit the scope of the invention as claimed.

Throughout the present description, the following abbreviations are used:

Abbreviations for unnatural amino acid residues:

N—Bzl—Gly:

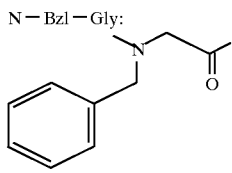

2Nal:

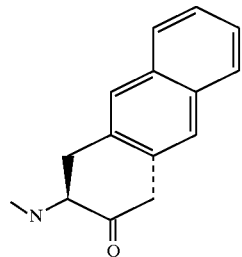

Aib:

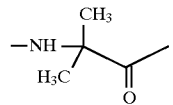

Abbreviations used for peptide bond substitutions:

ω(CH₂NH)

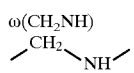

ω(CH₂NH₂)

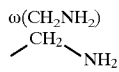

Abbreviations used for protecting groups:

Boc—

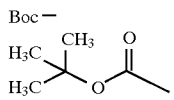

Fmoc—

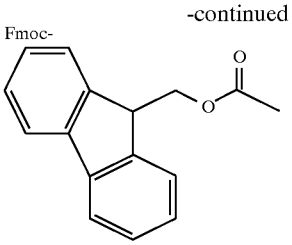

Cl—Z—

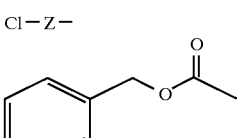

Bom—

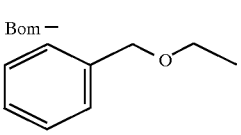

Adoc—

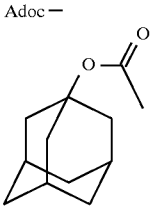

For—

EXAMPLE 1

H-His-D-Trpψ(CH₂NH)Ala-Trp-D-Phe-Lys-NH₂

The peptide resin H-Ala-Trp-D-Phe-Lys-Resin was synthesized according to the Fmoc strategy on an Applied Biosystems 431A peptide synthesizer in 0.25 mmol scale using the manufacturer supplied FastMoc UV protocols which employ HBTU ( 2-(1H-Benzotriazol-1-yl-)-1,1,3,3 tetramethyluronium hexafluorophosphate) mediated couplings in NMP (N-methyl pyrrolidone) and UV monitoring of the deprotection of the Fmoc protection group. The starting resin used for the synthesis was 470 mg 4-(2',4'-dimethoxyphenyl-Fmoc-aminomethyl)-phenoxy resin (Novabiochem AG Switzerland, cat. #:01-64-0013 ) having a substitution of 0.53 mmol/g . The protected amino acid derivatives used were Fmoc-Lys(Boc)-OH, Fmoc-D-Phe-OH, Fmoc-Trp-OH and Fmoc-Ala-OH.

The —CH₂NH— peptide bond isostere was introduced according to (Sasaki, Y. and Coy, D. H., PEPTIDES 8(1) 119–121. 1987.).

Fmoc-D-Trp-aldehyde was prepared from 399 mg of the corresponding N,O-dimethyl hydroxamate according to (Fehrentz, J. -A. and Castro. B., SYNTHESIS 676–678. 1983.) The crude aldehyde was dissolved in 8 ml 1% acetic acid in DMF (dimethyl formamide) and divided into two portions. The first portion was added to a stirred slurry of 400 mg (approx. 0.2 mmol) of H-Ala-Trp-D-Phe-Lys(Boc) -Resin in 8 ml 1% acetic acid in DMF at room temperature. Then 40 mg NaCNBH₃ (85% pure) dissolved in 1 ml DMF was added during 60 min and stirring was continued for further 60 min. After this the resin was isolated and washed with 1% acetic acid in DMF on a filter funnel. The resin was again suspended in 5 ml 1% acetic acid in DMF and the second portion of the Fmoc-Ala-aldehyde was added. Again 40 mg NaCNBH$_3$ (85% pure) dissolved in 1 ml DMF was added at room temperature during 60 min and the mixture was stirred for 18 h.

After this reductive alkylation step, the peptide resin was isolated and washed with 1% acetic acid in DMF on a filter funnel and the chain elongation was completed using the peptide synthesizer according to the above described procedures using the protected amino acid derivative Fmoc-His(Trt)-OH.

The peptide was cleaved from 240 mg of the peptide resin by stirring for 240 min at room temperature with a mixture of 3 ml TFA (triflouroacetic acid) , 225 mg phenol, 75 μl ethanedithiol, 150 μl thioanisole and 150 μl H$_2$O. The cleavage mixture was filtered and the filtrate was concentrated to an oil by a stream of nitrogen. The crude peptide was precipitated from this oil with 45 ml diethyl ether and washed 3 times with 45 ml diethyl ether.

The crude peptide was purified by semipreparative HPLC on a 25 mm×250 mm column packed with 7 μ C-18 silica. The column was equilibrated with 21% CH$_3$CN in 0.05M (NH$_4$)$_2$SO$_4$, which was adjusted to pH 2.5 with 4M H$_2$SO$_4$. After drying the crude peptide was dissolved in 5 ml 70% CH$_3$CN/0.1% TFA in H$_2$O and diluted to 50 ml with H$_2$O. 20 ml of this solution was diluted to 90 ml and injected on the column which then was eluted with a gradient of 21%–31% CH$_3$CN in 0.05M (NH$_4$)$_2$SO$_4$, pH 2.5 at 10 ml/min during 47 min at 40° C. The peptide containing fractions were collected and diluted with 3 volumes of H$_2$O and passed through a Sep-Pak C18 cartridge (Waters part. #:51910 ) which has been equilibrated with 0.1% TFA. It was then eluted with 70% CH$_3$CN containing 0.1% TFA and the purified peptide was isolated by lyophilisation after dilution of the eluate with water . The yield was 6.55 mg.

The final product obtained was characterised by amino acid analysis (peptide content and amino acid composition), analytical RP-HPLC (retention time) and by PDMS (Plasma desorption mass spectrometry)(molecular mass). Amino acid analysis and PDMS agreed with the expected structure within the experimental error of the method (PDMS: ±0.9 amu, Amino acid analysis ±10%).

The RP-HPLC analysis was performed using UV detection at 214 nm and a Vydac 218TP54 4.6mm×250mm 5 μ C-18 silica column (The Separations Group, Hesperia, USA) which was eluted at 1 ml/min at 42° C. Two different elution conditions were used:

A1: Equilibration of the column with 5% CH$_3$CN in a buffer consisting of 0.1M (NH$_4$)$_2$SO4, which was adjusted to pH 2.5 with concentrated H$_2$SO$_4$ and elution by a gradient of 5% to 60% CH$_3$CN in the same buffer during 50 min.

B1: Equilibration of the column with 5% CH$_3$CN/0.1% TFA/H$_2$O and elution by a gradient of 5% CH$_3$CN/0.1% TFA/H$_2$O to 60% CH$_3$CN/0.1% TFA/H$_2$O during 50 min.

The retention time using elution conditions A1 and B1 was found to be 22.01 min and 23.08 min respectively.

EXAMPLE 2

H-His-D-Trp-Ala-Trp-D-Pheψ(CH$_2$NH)Lys-NH$_2$

H-Lys(2-Cl-Z)-Resin was synthesized from 660 mg 4-methyl BHA resin (Bissendorf Biochemicals, Hannover, Germany. cat. #: RMIS50) having a substitution of 0.72 mmol/g and Boc-Lys(Cl-Z)-OH according to the Boc strategy on an Applied Biosystems 430A peptide synthesizer in 0.5 mmol scale using the manufacturer supplied single coupling protocols which employ single couplings with preformed symmetrical anhydrides in DMF. The protocols were modified to give 60 min coupling time.

The —CH$_2$NH— peptide bond isostere was introduced using a procedure similar to that described in Example 1. 675 mg of H-Lys(Cl-Z)-Resin and Boc-D-Phe-aldehyde prepared from 616 mg of the corresponding N,O-dimethyl hydroxamate was used.

After this reductive alkylation step, the resin was isolated and washed with 1% acetic acid in DMF on a filter funnel and the chain elongation was completed using the peptide synthesizer according to the above described procedures using the protected amino acid derivatives Boc-Trp(For)-OH, Boc-Ala-OH, Boc-D-Trp(For)-OH and Boc-His(Bom)-OH.

The peptide was cleaved from 391 mg of the peptide resin by stirring for 75 min with a mixture of 5 ml HF and 500 μl m-cresol. The HF was evaporated at 0° C. by a stream of nitrogen. The peptide was precipitated from the remaining oil together with the resin with 50 ml diethyl ether and washed 2 times with 50 ml diethyl ether and extracted from the resin with 2×2 ml TFA and precipitated from the combined TFA extract by 50 ml diethyl ether and washed 2 times with 50 ml diethyl ether.

After drying the formyl groups on the tryptophans were cleaved by dissolving and stirring the peptide in 64 ml 6M guanidinium hydrochloride containing 4 ml ethanolamine at 0° C. for 5 min. After this the mixture was neutralised by addition of 4 ml acetic acid and then diluted with 140 ml H$_2$O.

The crude peptide was purified by semipreparative. HPLC by direct injection of this reaction mixture on the column using a procedure similar to that described in Example 1. The yield was 20.6 mg.

The final product was characterised as described in Example 1.

RP-HPLC analysis using conditions A1 and B1 gave the retention times 21.28 min and 23.17 min respectively.

EXAMPLES 3–5

| Ex | Peptide | Prepared using a procedure similar to example no. | RP-HLPC retention time condition A1 (Ex. 1) | RP-HLPC retention time condition B1 (Ex. 1) |
|---|---|---|---|---|
| 3 | H-Hisψ(CH$_2$NH)D-Trp—Ala—Trp-D-Phe—Lys—NH$_2$ | 2 | 20.42 | 22.9 |
| 4 | H—His-D-Trp—Ala—Trpψ(CH$_2$NH)D-Phe—Lys—NH$_2$ | 1 | 18.97 | 21.3 |
| 5 | H—His-D-Trp—Alaψ(CH$_2$NH)Trp-D-Phe—Lys—NH$_2$ | 2 | 18.87 | 21.08 |

EXAMPLE 6

(2R)-(H-D-Ala-D-2Nal-Ala-Trp-NH)-3-phenylpropylamine

Fmoc-D-Phe-aldehyde was prepared from 385 mg of the corresponding N,O-dimethyl hydroxamate according to (Fehrentz, J. -A. and Castro. B., SYNTHESIS 676–678.

1983.) The crude aldehyde was dissolved in 20 ml 1% acetic acid in DMF and divided into two portions.

580 mg 4-(2',4'-dimethoxyphenyl-Fmoc-aminomethyl)-phenoxy resin (Novabiochem AG Switzerland, cat. #:01-64-0013) having a substitution of 0.43 mmol/g was deprotected with 20% piperidine in DMF for 20 min and washed with DMF and with 1% acetic acid in DMF.

The first portion Fmoc-D-Phe-aldehyde and 58 mg NaCNBH$_3$ (85% pure) dissolved in 1 ml DMF was added to the deprotected resin and the slurry was stirred a stirred at room temperature for 75 min. After this the resin was isolated on a filter funnel and washed with 1% acetic acid in DMF. The second portion of Fmoc-D-Phe-aldehyde together with 58 mg NaCNBH$_3$ (85% pure) dissolved in 1 ml DMF was added to the resin and the mixture was stirred a stirred at room temperature for 18 h and the resin was isolated on a filter funnel and washed with 1% acetic acid in DMF, with DMF, with DCM/methanol 6:4 and with DCM (dichloromethane).

Using this resin the chain elongation was completed using the peptide synthesizer according to the procedure described in example 1. and the protected amino acid derivatives Fmoc-Trp-OH, Fmoc-Ala-OH, Fmoc-D-2Nal-OH and Fmoc-D-Ala-OH.

The peptide was cleaved from 600 mg of the resulting peptide resin. The resulting crude peptide was dissolved in 50 ml H$_2$O and 25 ml of it was purified by semipreparative HPLC and characterised using procedures similar to those described in example 1. The yield was 10.9 mg.

RP-HPLC analysis using conditions A1 and B1 gave the retention times 27.98 min and 29.45 min respectively.

EXAMPLES 7–12

The protected peptide (2S)-((3-(1-Adoc-4-imidazolyl)propionyl)-D-Trp-Alaψ(CH$_2$NH)Trp-D-Phe-NH)-6-(Boc-amino)-hexanol was cleaved from 1800 mg of the 3-(1-Adoc-4-imidazolyl)propionyl-D-Trp-Alaψ(CH$_2$NH)Trp-D-Phe-Lys(Boc)-Sasrin resin by stirring the peptide resin for 24 h at room temperature with a mixture of 10.8 ml THF (tetrahydrofuran) 1.8 ml ethanol, 211 mg LiBr and 92 mg NaBH$_4$. Then 2 ml H$_2$O and 2 ml acetic acid were added dropwise. The resin beads were removed by filtration and washed with 25 ml ethanol. The filtrate was concentrated in vacuo and the remaining oil diluted with 50 ml H$_2$O and lyophilized. The resulting powder was subjected to TFA cleavage as described in example 1. ⅕ of the resulting crude peptide was purified as described in example 1. The yield was 28.54 mg.

The final product was characterized as described in Example 1. The retention time using elution conditions Al was found to be 20.4 min.

EXAMPLE 14

3-((3-(4-Imidazolyl)propionyl)-D-Trp-Alaψ(CH$_2$NH)Trp-D-Phe-NH)propylamine

The peptide resin (3-(1-Adoc-4-Imidazolyl)propionyl)-D-Trp-Alaψ(CH$_2$NH)Trp-D-Phe-Sasrin resin was synthesized in 1 mmol scale using a procedure similar to the one described in Example 1, with the exception that 1000 mg Sasrin resin (2-Methoxy-4-alkoxybenzyl alcohol resin) (Bachem, Bubendorf, Switzerland cat. #D-1295) with a substitution capacity of 0.87 mmol/g was used and that the protocol used for coupling of the first amino acid residue to the resin was the manufacturer-supplied 4-dimethylaminopyridine catalysed coupling of the preformed symmetrical anhydride followed by capping of residual —OH groups on the resin with benzoic anhydride.

| Ex | Peptide | Prepared using a procedure similar to example no. | RP-HLPC retention time condition A1 (Ex. 1) | RP-HLPC retention time condition B1 (Ex. 1) |
|---|---|---|---|---|
| 7 | H-D-Ala-D-2Nal—Ala—Trp-D-Pheψ(CH$_2$NH)Lys—NH$_2$ | 1 | 26.00 | 27.02 |
| 8 | H-D-Ala-D-Phe—Ala—Trp-D-Pheψ(CH$_2$NH)Lys—NH$_2$ | 1 | 22.02 | 23.30 |
| 9 | 3-(4-imidazolyl)propionyl-D-2Nal—Ala—Trp-D-Pheψ(CH$_2$NH)Lys—NH$_2$ | 1 | 26.33 | 27.70 |
| 10 | 3-(4-imidazolyl)acryloyl-D-2Nal—Ala—Trp-D-Pheψ(CH$_2$NH)Lys—NH$_2$ | 1 | 26.93 | 28.15 |
| 11 | (2S)-(H-D-Ala-D-2Nal—Ala—Trp-D-Phe—NH)-6-aminohexylamine | 6 | 25.33 | 26.08 |
| 12 | H-D-Ala-D-2Nal—Alaψ(CH$_2$NH)Trp-D-Phe—Lys—NH$_2$ | 1 | 23.62 | 25.07 |

EXAMPLE 13

(2S)-((3-(4-Imidazolyl)propionyl)-D-Trp-Alaψ(CH$_2$NH)Trp-D-Phe-NH)-6-aminohexanol The peptide resin 3-(1-Adoc-4-Imidazolyl)propionyl-D-Trp-Alaψ(CH$_2$NH)Trp-D-Phe-Lys(Boc)-Sasrin resin (Adoc is an abbreviation of 1-adamantyl-oxycarbonyl) was synthesized in 1 mmol scale using a procedure similar to the one described in Example 1 with the exception that 1020 mg Sasrin resin (2-Methoxy-4-alkoxybenzyl alcohol resin) (Bachem, Bubendorf, Switzerland cat. #D-1295) with a substitution capacity of 0.87 mmol/g was used and that the protocol used for coupling of the first amino acid residue to the resin was the manufacturer-supplied 4-dimethylaminopyridine catalysed coupling of the preformed symmetrical anhydride followed by capping of residual —OH groups on the resin with benzoic anhydride.

The peptide 3-((3-(1-Adoc-4-imidazolyl)propionyl)-D-Trp-Alaψ(CH$_2$NH)Trp-D-Phe-NH)propylamine was cleaved from 1000 mg of the (3-(1-Adoc-4-imidazolyl)propionyl)-D-Trp-Alaψ(CH$_2$NH)Trp-D-Phe-Sasrin by stirring for 20 h at room temperature with 10 ml of 1,3-diaminopropane. The spent resin was filtered off and extracted with 5 ml DMF. The combined filtrate and extract was slowly added to 240 ml 1M hydrochloric acid under stirring. The mixture was then diluted to 500 ml with H$_2$O and filtered.

The crude peptide was purified by in semipreparative HPLC in 9 runs by direct injection on the column of 9×⅕'th of this filtrate using a procedure similar to that described in example 1. The yield was 73.53 mg.

The final product was characterized as described in Example 1. The retention time using elution conditions A1 and B1 was found to be 21.5 min and 22.7 min, respectively.

EXAMPLE 15–18

| Ex | Peptide | Prepared using a procedure similar to example no. | RP-HLPC retention time condition A1 (Ex. 1) | RP-HLPC retention time condition B1 (Ex. 1) |
|---|---|---|---|---|
| 15 | (2R)-(H-D-2Nal—Ala—N—Bzl—Gly—NH)-3-phenylpropylamine | 6 | 29.6 | 31.2 |
| 16 | (2R)-(H-D-Ala-D-2Nal—Ala—N—Bzl—Gly—NH)-3-phenylpropylamine | 6 | 29.4 | 31.1 |
| 17 | H-D-Ala-D-2Nal—Ala—N—Bzl—Gly-D-Pheψ(CH$_2$NH)Lys—NH$_2$ | 2 | 30.5 | 31.7 |
| 18 | (2R)-(H-Aib-D-2Nal—Ala—N—Bzl—Gly—NH)-3-phenylpropylamine | 6 | 28.1 | 29.2 |

The structures of representative compounds of the invention are shown below:

3-((3-(4-Imidazolyl)propionyl)-D-Trp-Alaψ(CH$_2$NH)Trp-D-Phe-NH)propylamine

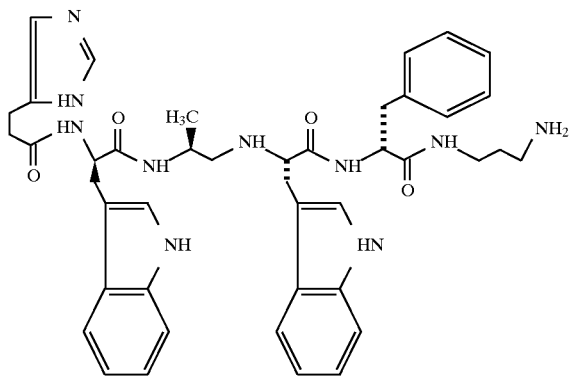

(2S)-((2R)-((3-(4-Imidazolyl)propionyl)-D-Phe-Ala-Trp-NH)-3phenylpropylamino)-6-aminohexanol

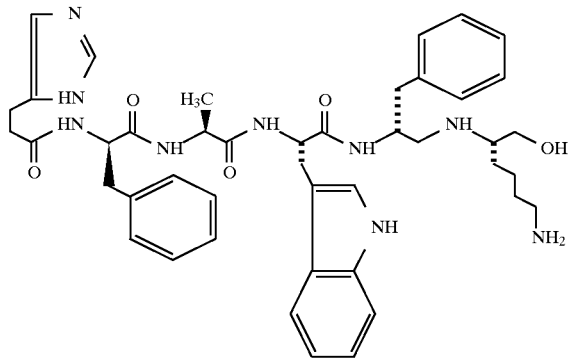

H—Aib—D—2Nal—Ala—N—Bzl—Gly—D—Pheω(CH$_2$NH$_2$)

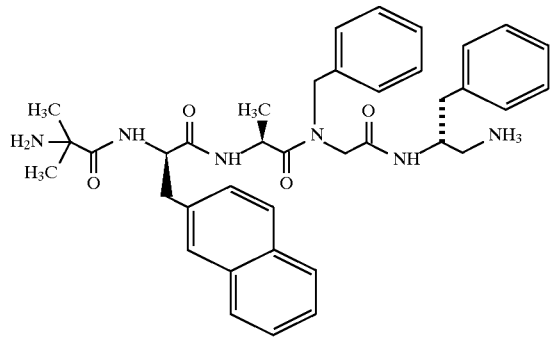

EXAMPLE 19

An in-vitro assay using rat pituitary cells was established to study the effect of different GH secretagogues. The mixed pituitary cell culture was isolated from the anterior pituitary of male rats and cultured for 3 days. After washing the cells were stimulated for 15 min and the amount of GH secreted measured in the culture supernatant.

The isolation of rat pituitary cells was a modification of Sartor, O. et al., *Endocrinology* 116, 1985, pp. 952–957. Pituitaries were discharged from 250 g male Sprague-Dawley rats after decapitation. The neurointermediate lobes were removed and the remainder was placed in Gey's medium supplemented with 0.25% glucose, 2× non essential amino acid and 1% BSA (isolation buffer). The glands were cut into small pieces and transferred to a flask containing 3 ml isolation buffer +11.5 mg trypsin and 1000 μg DNase and incubated for 35 min at 37° C., 95% O$_2$ and 70 rotations per min. The fragments were washed 3 times by sedimentation in isolation buffer and aspirated into single cells by using a pasteur pipet. After dispersion the cells were filtered though a nylon filter (160 μm) to remove undigested tissue. The cells were washed 3 times with isolation buffer supplemented with trypsin inhibitor (0.75 mg/ml) and resuspended in culture medium (DMEM supplemented with 25 mM HEPES, 4mM Glutamine, 0.75% sodium bicarbonate, 2.5% FCS, 3% horse serum, 10% rat serum, 1 nM T$_3$ and 40 μg/L dexamethasone) to a density of 2×10$^5$ cells/ml. The cells were seeded into microtiter plates, 200 μl/well and cultured for 3 days at 37° C. and 8% CO$_2$.

Following the culture period the cells were washed twice with stimulation buffer (HBSS supplemented with 1% BSA, 0.25% D-glucose and 25 mM HEPES) and preincubated for 1 hour. The buffer was then removed and new stimulation buffer containing a compound of the invention) was added and the plates were incubated for 15 min at 37° C. and 5% CO$_2$. The buffer was collected and analyzed for rat growth hormone (rGH) content in a scintillation proximity assay (SPA) as follows (SPA, essentially as described in U.S. Pat. No. 4,568,649, Hart and Greenwalt, *Mol.Immunol.* 16 1979, pp. 265–269, or Udenfriend et al., *Proc.Natl.Acad.Sci. USA* 82, 1985, pp. 8672–8676).

The rGH assay was performed in OptiPlates (96-well plates) suitable for direct counting in a Packards TopCount (β-scintillation counter).

Assay protocol:
40 μl buffer
10 μl sample (incubated stimulation buffer)
50 μl $^{125}$I-rGH
50 μl rabbit anti-rGH
50 μl SPA reagent (anti-rabbit antibody bound to fluomicrospheres)

The plates are sealed and placed on a plate shaker for 30 minutes followed by 10 hours of incubation, settling at 10°–15° C. and counting.

In the SPA, rGH bound to an anti-GH rabbit antibody (primary antibody) is reacted with a second antibody bound to fluomicrospheres (SPA Type II RIA available from Amersham). Any radiolabelled rGH which is bound to the primary antibody will be immobilized on the fluomicrospheres which will then produce light. Measurement in a β-scintillation counter makes it possible to calculate the amount of radiolabelled rGH. The amount of radiolabelled rGH bound to the fluomicrospheres decreases with an increasing content of rGH in the sample.

| Compound | $EC_{50}$ (nM) | $E_{max}$ (% of GHRP-6) |
|---|---|---|
| H—His-D-Trp—Ala—Trp-D-Phe—Lys—$NH_2$ | 2.0 | 100 |
| H-D-Ala-D-2Nal—Ala—Trp-D-Phe—Lys—$NH_2$ | 1.8 | 85 |
| H—His-DTrp-Ala—Trp-DPhe-ψ($CH_2NH$)Lys—$NH_2$ | 0.5 | 100 |
| H-DAla-D2Nal—Gly—Trp-DPhe—Lys—$NH_2$ | 0.8 | 75 |
| (2S)-((3-(4-Imidazolyl)propionyl)-D-Phe—Ala—Trp-D-Pheψ($CH_2NH$)-6-aminohexanol | 5 | 80 |

We claim:
1. A compound of general formula I

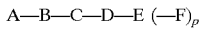

wherein
p is 0 or 1;
A is imidazolyl-$C_{1-6}$alkanoic acid, imidazolyl-$C_{1-6}$alkenoic acid, amino-$C_{1-6}$alkanoic acid or amino-$C_{1-6}$alkenoic acid or a L- or D- α-amino acid selected from the group consisting of H-His, H-Ala, H-D-Ala, H-β-alanine, H-amino-isobutyric acid, sarcosine and Gly;
B is D-Trp, D-2Nal or D-Phe;
C is Ala, Ser or Gly;
D is Trp, Phe, β-(2-Thienyl)-alanine or N-aralkyl glycine;
E, when p is 1, is D-Phe, or, when p is 0, E is —NH—CH($CH_2$—$R^3$)—CO—$R^4$ or —NH—CH($CH_2$—$R^3$)—$CH_2$—$R^4$, wherein
$R^3$ is phenyl,
and $R^4$ is piperazino, morpholino, piperidino, —OH or —N($R^5$)$R^6$, wherein each of $R^5$ and $R^6$ is independently hydrogen or lower alkyl;
F, when p is 1, is —NH—CH($R^{10}$)—($CH_2$)$R^7$, wherein
v is 0 or an integer between 1 and 8, and
$R^7$ is imidazolyl, piperazino, morpholino, piperidino or —N($R^8$)—$R^9$, wherein each of $R^8$ and $R^9$ is independently hydrogen or lower alkyl, or the Amadori rearrangement product from an amino group and a hexapyranose or a hexapyranosyl-hexapyranose,

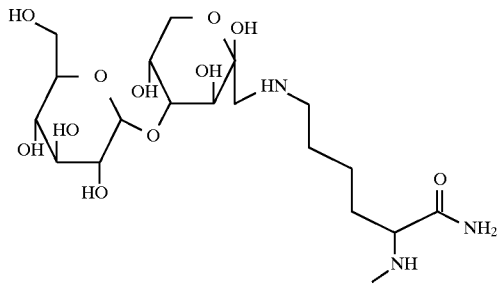

and
$R^{10}$ is —H, —COOH, —CO—$R^{11}$, $CH_2$—$R^{11}$ or —$CH_2$—OH, wherein $R^{11}$ is piperazino, morpholino, piperidino or —N($R^{12}$)—$R^{13}$, wherein each of $R^{12}$ and $R^{13}$ is independently hydrogen or lower alkyl;
with the proviso that at least one amide bond between A and B, B and C, C and D, D and E or, when p is 1, E and F, is substituted by aminomethylene or that, when p is 0, E is —NH—CH($CH_2$—$R^3$)—CH—$R^4$ or that, when p is 1, $R^{10}$ is $CH_2$—$R^{11}$;
or a pharmaceutically acceptable salt thereof.

2. A compound according to claim 1, wherein p is 1.

3. A compound according to claim 1, wherein A is H-His, H-D-Ala or imidazolyl propionic acid.

4. A compound according to claim 1, wherein B is D-Trp or D-2Nal.

5. A compound according to claim 1, wherein C is Ala.

6. A compound according to claim 1, wherein D is N-benzyl glycine or Trp.

7. A compound according to claim 1, wherein E is D-Phe.

8. A compound according to claim 1, wherein v=6 and $R^7$=—$NH_2$.

9. A compound according to claim 1, wherein $R^{10}$ is $CONH_2$, or —$CH_2$—OH..

10. A compound according to claim 1 selected from the group consisting of
H-Hisψ($CH_2NH$)D-Trp-Ala-Trp-D-Phe-Lys-NH,
H-His-D-Trpψ($CH_2NH$)Ala-Trp-D-Phe-Lys-$NH_2$
H-His-D-Trp-Alaψ($CH_2NH$)Trp-D-Phe-Lys-$NH_2$
H-His-D-Trp-Ala-Trpψ($CH_2NH$)D-Phe-Lys-$NH_2$
H-His-D-Trp-Ala-Trp-D-Pheψ($CH_2NH$)Lys-$NH_2$
H-D-Ala-D-2Nal-Alaψ($CH_2NH$)Trp-D-Phe-Lys-$NH_2$
H-D-Ala-D-2Nal-Ala-Trp-D-Pheψ($CH_2NH$)Lys-$NH_2$
(3-(4-Imidazolyl)propionyl)-D-2Nal-Ala-Trp-D-Pheψ($CH_2NH$)Lys-OH
(3-(4-Imidazolyl)propionyl)-D-2Nal-Ala-Trp-D-Pheψ($CH_2NH$)Lys-$NH_2$
(3-(4-Imidazolyl)acryloyl)-D-2Nal-Ala-Trp-D-Pheψ($CH_2NH$)Lys-$NH_2$
H-D-Ala-D-Phe-Ala-Trp-D-Pheψ($CH_2NH$)Lys-$NH_2$
(2R)-(H-D-Ala-D-Phe-Ala-Trp-NH)-3-phenylpropylamine
(2S)-(H-D-Ala-D-2Nal-Alaψ($CH_2NH$)Trp-D-Phe-NH)-6-aminohexanol
H-D-Ala-D-2Nal-Alaψ($CH_2NH$)Trp-D-Phe-$NH_2$
4-(H-D-Ala-D-2Nal-Alaψ($CH_2NH$)Trp-D-Phe-NH)butylamine
(2R)-(H-D-Ala-D-2Nal-Ala-Trp-NH)-3-phenylpropylamine
((2R)-(H-D-Ala-D-2Nal-Ala-Trp-NH)-3-phenylpropylamino)hexylamine
(2R)-(H-D-2Nal-Ala-N-Bzl-Gly-NH)-3-phenylpropylamine
(2R)-(H-D-Ala-D-2Nal-Ala-N-Bzl-Gly-NH)-3-phenylpropylamine
H-Aib-D-2Nal-Ala-N-Bzl-Gly-D-Pheψ($CH_2NH$)Lys-$NH_2$
(2S)-((3-(4-Imidazolyl)propionyl)ψ($CH_2NH$)D-Phe-Ala-Trp-D-Phe-NH)-6-aminohexanol
(2S)-((3-(4-Imidazolyl)propionyl)-D-Pheψ(CHNH)Ala-Trp-D-Phe-NH)-6-aminohexanol
(2S)-((3-(4-Imidazolyl)propionyl)-D-Phe-Alaψ($CH_2NH$)Trp-D-Phe-NH)-6-aminohexanol
(2S)-((3-(4-Imidazolyl)propionyl)-D-Phe-Ala-Trpψ($CH_2NH$)D-Phe-NH)-6-aminohexanol (2S)-(2R)-((3-(4-Imidazolyl)propionyl)-D-Phe-Ala-Trp-NH)-3-phenylpropylamino)-6-aminohexanol 3-((3-(4-Imidazolyl)propionyl)-D-Trp-Ala-ψ(CH$_2$NH)Trp-D-Phe-NH)propylamine (2S)-((3-(4-Imidazolyl)propionyl)-D-Phe-Ala-Trp-D-Pheψ(CH$_2$NH)NH)-6-aminohexanol (2S)-((3-(4-Imidazolyl)propionyl)-D-Trp-Alaψ(CH$_2$NH)Trp-D-Phe-NH)-6-aminohexanol 3-((3-(4-Imidazolyl)propionyl)-D-Trp-Alaψ(CH$_2$NH)Trp-D-Phe-NH)propylamine H-D-Ala-D-2Nal-Ala-N-Bzl-Gly-D-Pheψ(CH$_2$NH)-Lys-NH$_2$ and H-Aib-D-2Nal-Ala-N-Bzl-Gly-D-Pheψ(CH$_2$NH$_2$).

11. A pharmaceutical composition comprising an effective amount of a compound according to claim 1 together with a pharmaceutically acceptable carrier or diluent.

12. A composition according to claim 11 in unit dosage form, wherein the effective amount is in the range from about 10 to about 200 mg.

13. A pharmaceutical composition for stimulating the release of growth hormone from the pituitary, comprising an effective amount of a compound according to claim 1 together with a pharmaceutically acceptable carrier or diluent.

14. A method of stimulating the release of growth hormone from the pituitary, comprising administering to a subject in need thereof an effective amount of a compound according to claim 1.

15. A method according to claim 14, wherein the effective amount is in the range of from about 0.0001 to about 100 mg/kg body weight per day.

* * * * *

UNITED STATES PATENT AND TRADEMARK OFFICE

CERTIFICATE OF CORRECTION

PATENT NO. : 5,854,211

DATED : December 29, 1998

INVENTOR(S) : Johansen et al.

It is certified that error appears in the above-identified patent and that said Letters Patent is hereby corrected as shown below:

Col. 15, line 45, claim 1, delete "-($CH_2$)$R^7$-" and insert ---($CH_2$)$_v$-$R^7$)---

Col. 16, line 6, claim 1, delete "-CH-$R^4$" and insert -- -$CH_2$-$R^4$—

Col. 16, line 62, claim 10 delete "(CHNH)" and insert $CH_2$NH)

Signed and Sealed this

Twenty-first Day of November, 2000

Attest:

Q. TODD DICKINSON

*Attesting Officer*     *Director of Patents and Trademarks*